US011395591B2

(12) United States Patent
Yu et al.

(10) Patent No.: US 11,395,591 B2
(45) Date of Patent: Jul. 26, 2022

(54) SYSTEM INTEGRATING VIDEO COMMUNICATION AND PHYSICAL SIGN ANALYSIS

(71) Applicant: Joyware Electronics Co., Ltd., Zhejiang (CN)

(72) Inventors: Jie Yu, Zhejiang (CN); Jiangfeng Yu, Zhejiang (CN); Weiping Zhu, Zhejiang (CN); Xugang Shi, Zhejiang (CN)

(73) Assignee: Joyware Electronics Co., Ltd., Hangzhou (CN)

( * ) Notice: Subject to any disclaimer, the term of this patent is extended or adjusted under 35 U.S.C. 154(b) by 328 days.

(21) Appl. No.: 16/838,008

(22) Filed: Apr. 1, 2020

(65) Prior Publication Data
US 2020/0229699 A1 Jul. 23, 2020

Related U.S. Application Data

(63) Continuation of application No. PCT/CN2019/096715, filed on Jul. 19, 2019.

(30) Foreign Application Priority Data

Oct. 8, 2018 (CN) .......................... 201811166541.6

(51) Int. Cl.
*A61B 5/00* (2006.01)
*A61B 5/02* (2006.01)
(Continued)

(52) U.S. Cl.
CPC .............. *A61B 5/0044* (2013.01); *A61B 5/02* (2013.01); *G06V 40/15* (2022.01); *G06V 40/164* (2022.01);
(Continued)

(58) Field of Classification Search
CPC ..... A61B 5/0044; A61B 5/02; A61B 2503/08; A61B 5/1176; A61B 5/021; A61B 5/024;
(Continued)

(56) References Cited

U.S. PATENT DOCUMENTS 8,475,367 B1 * 7/2013 Yuen .................... A61B 5/0205
177/4
8,529,409 B1 * 9/2013 Lesea-Ames .......... G16H 40/63
482/8
(Continued)

FOREIGN PATENT DOCUMENTS

| CN | 204031329 U | 12/2014 |
|---|---|---|
| CN | 105996993 A | 10/2016 |

(Continued)

OTHER PUBLICATIONS

International search report of PCT Patent Application No. PCT/CN2019/096715 dated Sep. 27, 2019.

*Primary Examiner* — Wesley J Tucker

(57) ABSTRACT

The present invention discloses a system integrating video communication and physical sign analysis, comprising at least one front-end device. The front-end device comprises a camera device, a display device, an audio device, a button device and a processor. The camera device, the display device, the audio device and the button device are all connected to the processor, and the processor can connect to the Internet network and the mobile device via wired or wireless means. The front-end device and the mobile device can perform video communication, and the front-end device can perform physical sign analysis according to the images collected by the camera device. Based on some applications in the prior art, the present invention combines video collection technology and human face analysis technology to perform physical sign analysis and obtain related indexes.

10 Claims, 8 Drawing Sheets

(51) Int. Cl.
*G06V 40/16* (2022.01)
*G06V 40/10* (2022.01)
*G06V 40/70* (2022.01)
*G06Q 20/40* (2012.01)

(52) U.S. Cl.
CPC .......... *G06V 40/166* (2022.01); *G06V 40/168* (2022.01); *G06V 40/171* (2022.01); *G06V 40/172* (2022.01); *G06V 40/174* (2022.01); *G06Q 20/4012* (2013.01); *G06V 40/70* (2022.01)

(58) Field of Classification Search
CPC ..... A61B 5/0816; A61B 5/165; A61B 5/7267; A61B 5/0022; G06V 40/15; G06V 40/164; G06V 40/166; G06V 40/168; G06V 40/171; G06V 40/172; G06Q 20/4012; G16H 40/63; G16H 40/67; G16H 50/30; H04L 67/141; H04L 67/16; H04M 1/72403; H04N 5/23219; H04N 7/141
See application file for complete search history.

(56) References Cited

U.S. PATENT DOCUMENTS

| | | | |
|---|---|---|---|
| 9,750,420 B1* | 9/2017 | Agrawal | G06T 7/73 |
| 2013/0012790 A1* | 1/2013 | Horseman | A61B 5/6891 |
| | | | 600/301 |
| 2014/0121540 A1* | 5/2014 | Raskin | A61B 5/0077 |
| | | | 600/479 |
| 2017/0105662 A1* | 4/2017 | Silawan | A61B 5/0077 |
| 2017/0249823 A1* | 8/2017 | Espinoza | G08B 21/0446 |
| 2017/0367590 A1* | 12/2017 | Sebe | G06V 40/176 |
| 2019/0147223 A1* | 5/2019 | Chen | G06V 40/169 |
| | | | 382/165 |
| 2019/0343457 A1* | 11/2019 | Rahmani | G06N 3/08 |
| 2020/0163560 A1* | 5/2020 | Chang | G06V 40/171 |
| 2020/0214614 A1* | 7/2020 | Rundo | G06N 3/0445 |
| 2020/0234036 A1* | 7/2020 | Yu | G06V 20/46 |

FOREIGN PATENT DOCUMENTS

| | | |
|---|---|---|
| CN | 106725410 A | 5/2017 |
| WO | 2018085945 A1 | 5/2018 |

* cited by examiner

| Client identification number | Client IP | Client status |
|---|---|---|
| Unique string | IP address | Standby/in call/ calling |

SYSTEM INTEGRATING VIDEO COMMUNICATION AND PHYSICAL SIGN ANALYSIS

CROSS REFERENCE TO RELATED APPLICATIONS

The present application is a Continuation Application of PCT Application No. PCT/CN2019/096715 filed on Jul. 19, 2019, which claims the benefit of Chinese Patent Application No. 201811166541.6 filed on Oct. 8, 2018. All the above are hereby incorporated by reference. the contents of which are incorporated herein by reference in their entirety.

FIELD OF THE INVENTION

The present invention relates to the field of video communication and human face analysis techniques.

BACKGROUND OF THE INVENTION

With the development of technology, the civilian cameras have been gradually used in families. Users can initiate real-time video viewing of the camera through a mobile APP, and the mobile APP can also initiate a video call with the camera. However, there are no comprehensive front-end devices suitable for elderly families available on the markets that can set a key to communicate with the preset family's mobile APP, and no devices and methods for the front-end device to collect human face video clips for physical sign analysis.

SUMMARY OF THE INVENTION

The present invention aims to overcome the shortcomings of the prior art and provide a system integrating video communication and physical sign analysis.

To achieve the object, the present invention adopts the following technical solutions:

A system integrating video communication and physical sign analysis, comprising:

at least one front-end device, and the front-end devices may be configured to receive other devices or external data and/or signals. In some preferred embodiments, the front-end device may directly receive external data and/or signals, in some preferred embodiments, the front-end device may receive external data and/or signals indirectly through other devices, in some preferred embodiments, the front-end device may receive at least one type of data and/or signals, in some preferred embodiments, the front-end device may directly process the received data and/or signals, in some preferred embodiments, the front-end device may process the received data and/or signals through other devices, in some preferred embodiments, the front-end device may comprise a data and/or signal processing device, in some preferred embodiments, the data and/or signal processing device may be a processor, in some preferred embodiments, the front-end device may further comprise a camera device, a display device, an audio device, and/or a button device, in some preferred embodiments, the camera device, the display device, the audio device and the button device may all be connected to the processor, in some preferred embodiments, the processor may be connected to the Internet network wiredly or wirelessly.

In some preferred embodiments, the system of the present invention may further comprise a mobile device, in some preferred embodiments, a mobile device is capable of interconnecting with the front-end device and establishing data communication, in some preferred embodiments, the mobile device may establish data communication with one or more of the front-end devices, in some preferred embodiments, the mobile device can establish interconnection with other front-end devices through one of the front-end devices, in some preferred embodiments, the mobile device may receive the data and/or signals of other front-end devices through a front-end device, in some preferred embodiments, the mobile device may receive data and/or signals of a plurality of front-end devices directly at the same time.

In some preferred embodiments, the front-end device and the mobile device may achieve video communication, and the front-end device can perform the physical sign analysis according to the images collected by the camera device. In some preferred embodiments, the mobile device may send the collected images to the front-end device for physical sign analysis. In some preferred embodiments, the front-end device may perform physical sign analysis on the image collected by itself.

Further, the button device comprises a preset button and a physical sign analysis trigger button. In some preferred embodiments, the physical sign analysis can be triggered by a button. In this way, the physical sign analysis is not carried out automatically. In some preferred embodiments, the physical sign analysis can be triggered automatically. In this way, the physical sign analysis may be preset; in some preferred embodiments, the physical sign analysis may be manually and selectively triggered by a button.

Further, the camera device is a conventional camera having a certain resolution. In some preferred embodiments, the camera device may be a conventional camera with a resolution of less than 200 W. For example, in some preferred embodiments, the camera device may adopt a 1080P camera. Of course, a camera with a resolution greater than 200 W may be used as required. In some preferred embodiments, the camera device may adopt a binocular camera. In some preferred embodiments, the camera device may adopt an IP camera.

Further, the display screen is an ordinary display screen or a touch display screen. In some preferred embodiments, a CRT display screen is used, in some preferred embodiments, a LCD display screen is used, in some preferred embodiments, a touch display screen may be a vector pressure sensing technology touch screen, a resistance technology touch screen, a capacitance technology touch screen, an infrared technology touch screen and/or a surface acoustic wave technology touch screen.

Further, the process for the front-end device to perform physical sign analysis comprises:

(1) capturing the video by the camera device and sending to the processor, and displaying on the display device;

(2) performing human face detection analysis of the captured video frame by frame by the processor, and acquiring the largest human face close to the middle position of the video only;

(3) positioning the coordinates of several feature points for the human face detected by each frame by algorithm;

(4) extracting pixel RGB values of the area enclosed by several feature points for the human face image of each frame of the face in a time slice and performing time series analysis to form physical sign analysis waveform data;

(5) sending the physical sign analysis waveform data and the human face images to the physical sign analysis service for deep learning of the relevant physical index indexes to obtain the relevant physical sign indexes of the person.

In some preferred embodiments, physical sign indexes include a certain part of a human body that may be different from other human bodies, such as the head, the legs, in some preferred embodiments, physical signs indexes may include an element of a human body that may be different from other human bodies, such as the size of the head, the length of the legs, and the height of the human body, etc. In some preferred embodiments, physical sign indexes may be elements that are easily identified in image recognition; in some preferred embodiments, physical sign indexes may be a single element or a combination of elements. In some preferred embodiments, the recognition priority of the physical sign indexes may be set, for example, recognizing some elements in priority, for example, the eye size. When a human body cannot be distinguished from other human bodies by these elements, other elements may be further recognized, and so forth.

Further, a process of recording the physical sign indexes is included, specifically, comparing the current human face with the customer group face database to obtain the customer number, and recording the physical sign indexes obtained in the step (5) in the physical sign data record sheet of the customer number.

Further, the initiator of the video communication is a front-end device or a mobile device. In some preferred embodiments, the front-end device initiates a video communication request, in some preferred embodiments, the front-end device initiates a video communication request by using another device, in some preferred embodiments, the front-end device initiates a video communication request to the mobile device actively and establishes a communication with the mobile device, in some preferred embodiments, the mobile device initiates a video communication request to the front-end device actively, and establishes a communication with the front-end device to perform information interaction.

Further, during video communication, the front-end device or mobile device is the client of the video communication, and the client registers and maintains the registration status on the video communication. In some preferred embodiments, the client firstly completes the registration on the video communication, and then performs video communication, in some preferred embodiments, the video communication means that the front-end device or the mobile device records video and perform communication of the recorded video via data or other ways, in some preferred embodiments, the recorded video can be transmitted during the communication process.

Further, the registration process of the client comprises:

(1) assigning each client a unique client identification number; in some preferred embodiments, the identification number may be a string of characters, in some preferred embodiments, the identification number may be a code having security function, for example, an identification number that needs to be verified, in some preferred embodiments, the identification number may not include security certification information.

(2) initiating a registration application to the video communication service cloud when the client is running, and the registration application including registration information such as the client identification number and the client IP address of the current client; in some preferred embodiments, the registered client has a uniquely identifiable identity on the video communication service cloud, in some preferred embodiments, once the client is registered on the video communication service cloud, its registration information can be queried, in some preferred embodiments, the video/information/data sent by the client can be queried through the registration information.

(3) generating a client status table by the video communication service cloud according to the registration information; in some preferred embodiments, the client status table may include information of the client, in some preferred embodiments, the client status table may also include the status of the client, for example, whether the client is online, or whether the client is offline, or the duration of online of the client, or the duration of offline of the client, etc.

(4) periodically sending heartbeat information to the video communication service cloud by the client, and refreshing the client status table by the video communication service cloud after receiving the heartbeat information.

Further, the process of initiating video communication by the client comprises:

(1) configuring a contact list on the client and binding a button to the contact persons in the contact list;

(2) initiating a video communication connection request to another client through the video communication service cloud by the current client;

(3) feeding back the current status information by another client, and feeding back the information of connection failure if the current status is in the call or during the call; and feeding back the information such as the IP address if the current status is no answer.

The present invention can achieve the following beneficial effects. Based on some applications in the prior art, the present invention combines video collection technology and human face analysis technology to perform physical sign analysis and obtain related indexes. In addition, the invention provides one-to-one or one-to-more video communication services for all registered clients through the video communication service cloud, and connects any two clients via the video communication service cloud to facilitate the interconnection of a front-end device and a mobile app. The elderly or children who use the front-end device may directly connect with adult's mobile phone app via this service, to facilitate communication; moreover, the front-end device may also analyze the physical signs of the smart device users through the video collected by the camera device, and send these physical sign information to the mobile phone app via the communication services such that the users of mobile phone app can know them at any time.

DETAILED DESCRIPTION

The technical solutions of the present invention are further described in detail below with reference to the accompanying drawings. It should be noted that the embodiments are merely illustrative of the invention and are not intended to limit the invention.

Figure 1:
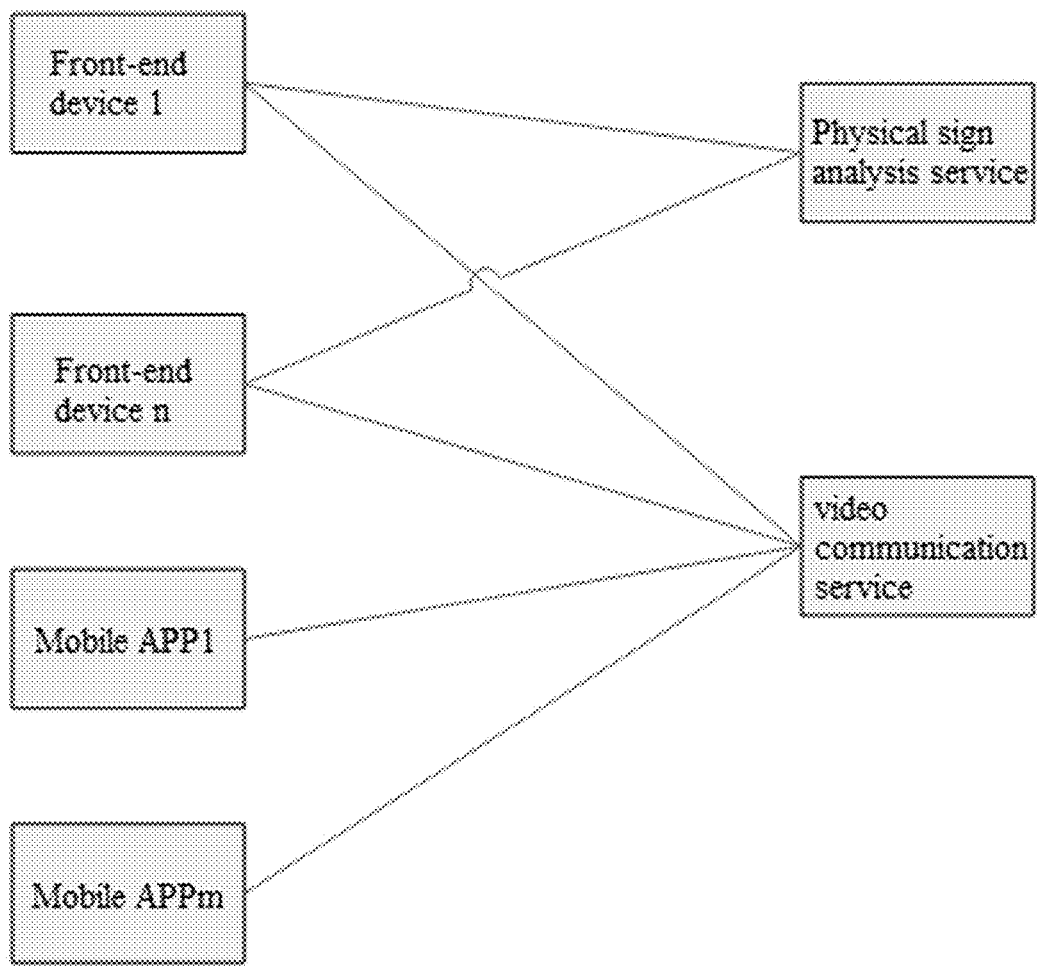
FIG. 1 is an overall structural view of the present invention.

Referring to FIG. 1, the present invention provides a system integrating video communication and physical sign analysis, comprising: at least one front-end device and at least one mobile device. Two front-end devices and two mobile devices are shown in the figure. The front-end devices are respectively connected to the physical sign analysis service, and the front-end device may collect video and perform corresponding physical sign analysis according to the face recognition in the video. The front-end devices are further connected to the video communication service, and the mobile device is also connected to the video communication service respectively, that is, the front-end device and the mobile device can perform video communication through the video communication service.

Figure 2:
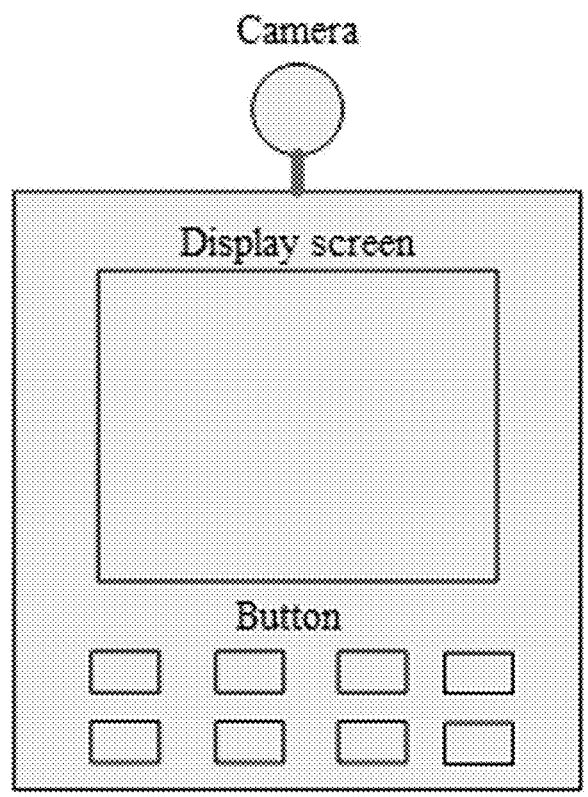
FIG. 2 is a schematic diagram of a front-end device.

As shown in FIG. 2, the front-end device comprises a camera device, a display device, an audio device, a button device and a processor. The camera device, the display device, the audio device and the button device are all connected to the processor, and the processor can connect to the Internet network via wired or wireless means, of which, the processor is used for physical sign analysis and also for signal interaction with a video communication.

In a front-end device, the button device comprises a preset button and a physical sign analysis trigger button. The button can be a physical button, or a virtual button set on the touch display screen. The preset button can be used to set a parameter value, to correspond to the parameter value directly by pressing the button, and the physical sign analysis trigger button is set. Physical sign analysis can be performed by pressing or touching this button, which makes the physical sign analysis to become an optional mode. The camera device is a conventional camera with a certain resolution (for example, 720p, 1080p or higher resolution). The display screen may be an ordinary display screen with different resolutions, or a display screen that can be displayed only, or a touch display screen that can be touch-operated.

Figure 3:
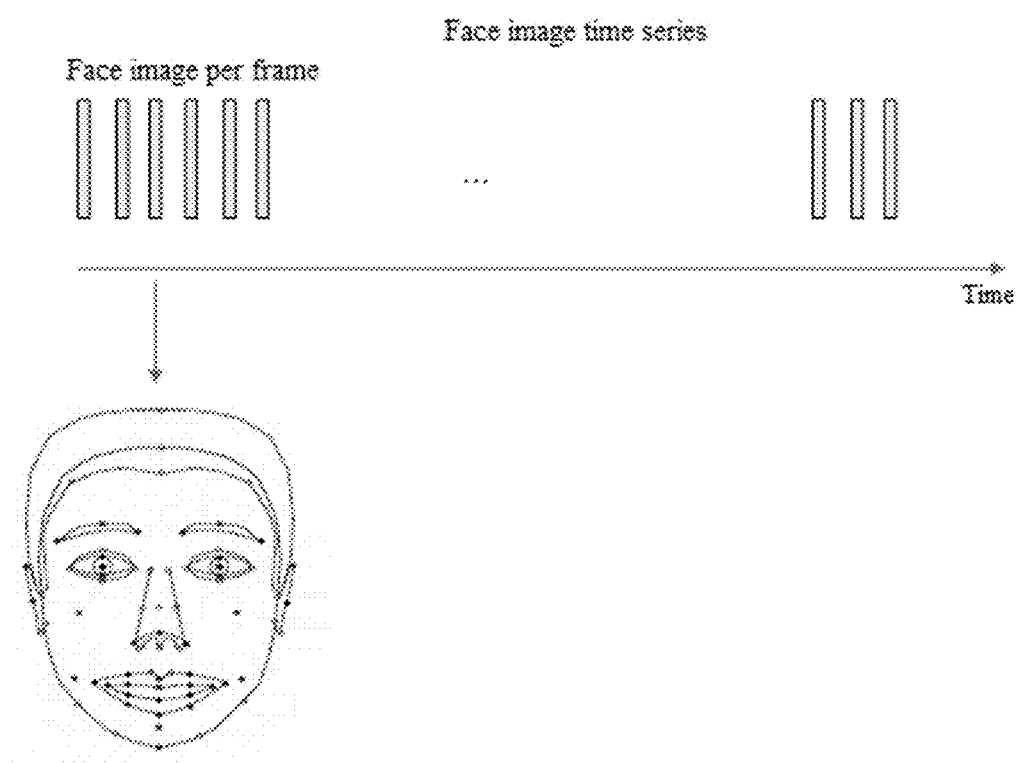
FIG. 3 is a schematic diagram of human face acquisition.

As shown in FIG. 3, it shows a process in which a front-end device captures video through a camera and divides the video.

Specifically, the front-end device captures video through the camera and displays it on the display screen, and the program running on the processor of the front-end device performs face detection on the captured video frame by frame. If only one face is analyzed, the face image is collected as the basis for analysis of human face; and if multiple faces are detected, the largest human face close to the middle position of the video is taken, and the coordinates of several feature points for the human face detected by each frame are positioned by algorithm, and then the pixel RGB values of the area enclosed by several feature points for the human face image of each frame of the face in a time slice are extracted and time series analysis is performed to form physical sign analysis waveform data. The time slice can be arbitrarily set, for example, 10 s, 30 s, several minutes, the number of video frames per second can be 25 or 30, in an average distribution. The feature points of the human face are determined according to the physical sign analysis needs. The selection of feature points can be determined as required, for example, some feature points shown in the face part in FIG. 3, which may include feature points of eyes, mouth and ears, etc. Different feature points can be used to detect different physical sign indexes as needed. According to the physical sign analysis waveform data, the related physical sign indexes of the person are obtained. The physical index indexes include heart rate, respiratory rate, psychological pressure and blood pressure, etc.

In some preferred embodiments, the color of the pixel is RGB color, in some preferred embodiments, the pixels of the images can be represented by red, green, and blue or a combination thereof respectively. In some preferred embodiments, in terms of numbers, each color may be represented by 8 bit or 16 bit respectively.

In some preferred embodiments, physical sign indexes may further include a certain part of a human body that may be different from other human bodies, for example, the head, the legs, in some preferred embodiments, physical sign indexes may include an element of a human body that may be different from other human bodies, for example, the size of the head, the length of the legs, the height of human body, etc. In some preferred embodiments, physical sign indexes may be elements that are easily identified in image recognition; in some preferred embodiments, physical sign indexes may be a single element or a combination of elements. In some preferred embodiments, the recognition priority of the physical sign indexes may be set, for example, recognizing some elements in priority, for example, the eye size. When a human body cannot be distinguished from other human bodies by these elements, other elements may be further recognized, and so forth.

The sign analysis service has a deep learning algorithm inside, and relevant deep learning modeling and a large number of sample learning are carried out according to the physical sign indexes that need to be detected in advance.

The video communication service is responsible for video communication bridging between a front-end device and a front-end device or between a front-end device and a mobile app.

The initiator of the video communication service may be a front-end device or a mobile APP. The front-end device and the mobile app need to register and remain registration status in the video communication service in real time. Video communication can be initiated in both directions between the front-end device and the front-end device or between the front-end device and the mobile app through the video communication service cloud.

Figures 4, 5:
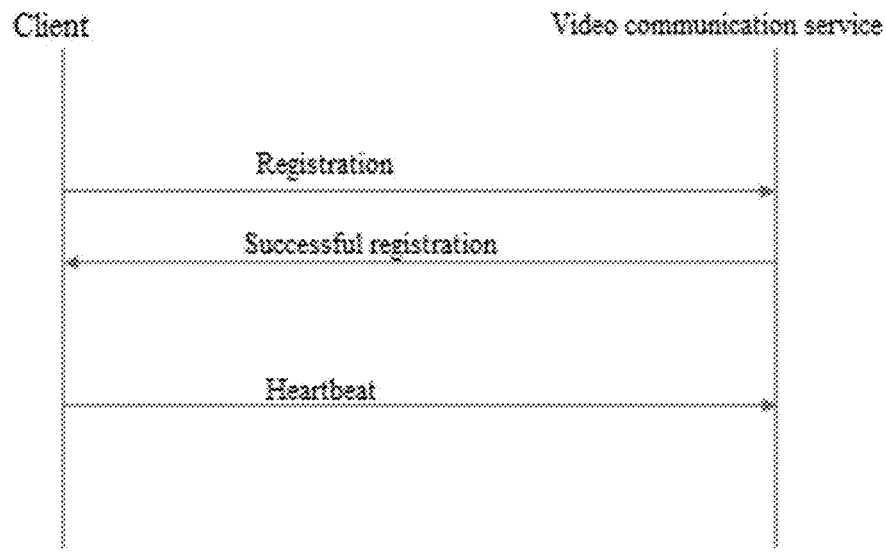
FIG. 4 is a schematic diagram of a client status table.
FIG. 5 is a flow diagram showing the registration of a client on a video communication service cloud.

Both the front-end device and the mobile app can be used as the client. FIG. 5 shows the registration process of the client on the video communication service cloud, comprising:

(1) assigning each client a unique client identification number;

(2) initiating a registration application to the video communication service cloud when the client is running (the front-end device is energized or the mobile app is running), and the registration application including registration information such as the client identification number and the client IP address of the current client;

(3) generating a client status table as shown in FIG. 4 by the video communication service cloud according to the registration information;

(4) periodically sending heartbeat information through which the video communication service cloud indicates that the client is always in a registration status, to the video communication service cloud by the client, and refreshing the client status table by the video communication service cloud after receiving the heartbeat information.

Figure 6:
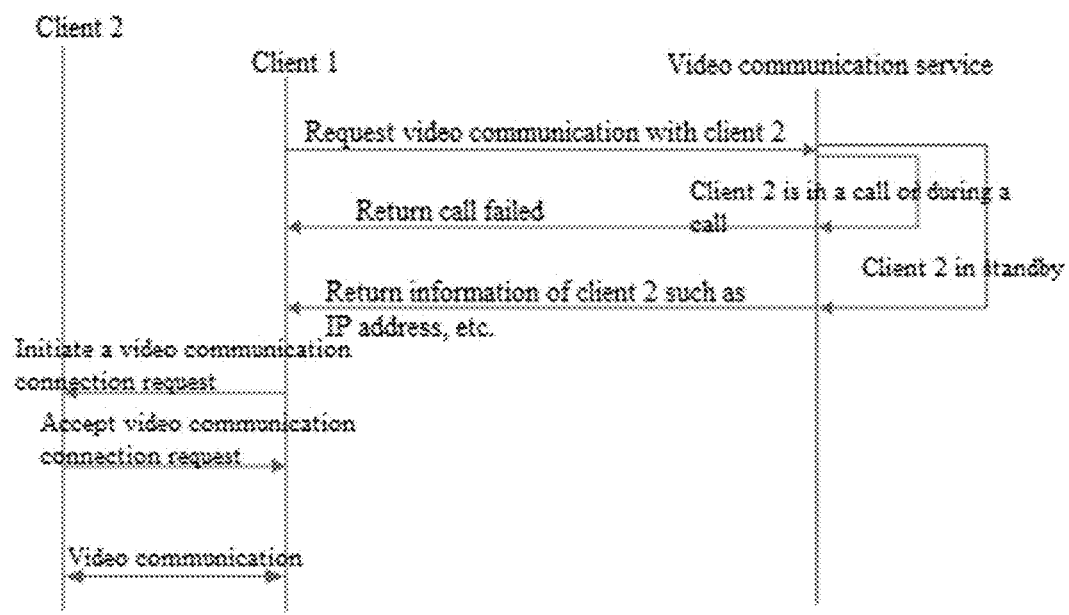
FIG. 6 is a flow diagram showing initiating a video communication by a client.

FIG. 6 shows the process of the client to initiate video communication, comprising:

(1) configuring a contact list on the client and binding a button to the contact persons for the front-end device, that is, pressing a button to initiate a video communication request to the contact preset by the button.

(2) initiating a video communication connection request to another client through the video communication service cloud by the current client. The video communication connection request is transmitted through the video communication service cloud;

(3) feeding back the current status information by another client, and if the current status is in the call or during the call, feeding back the information of connection failure to the video communication service cloud, and the information of connection failure being sent to the client that initiates the video communication request by the video communication service cloud; and feeding back the information such as the IP address if the current status is no answer, and the information such as the IP address being sent to the client that initiates the video communication request by the video communication service cloud.

Figure 7:
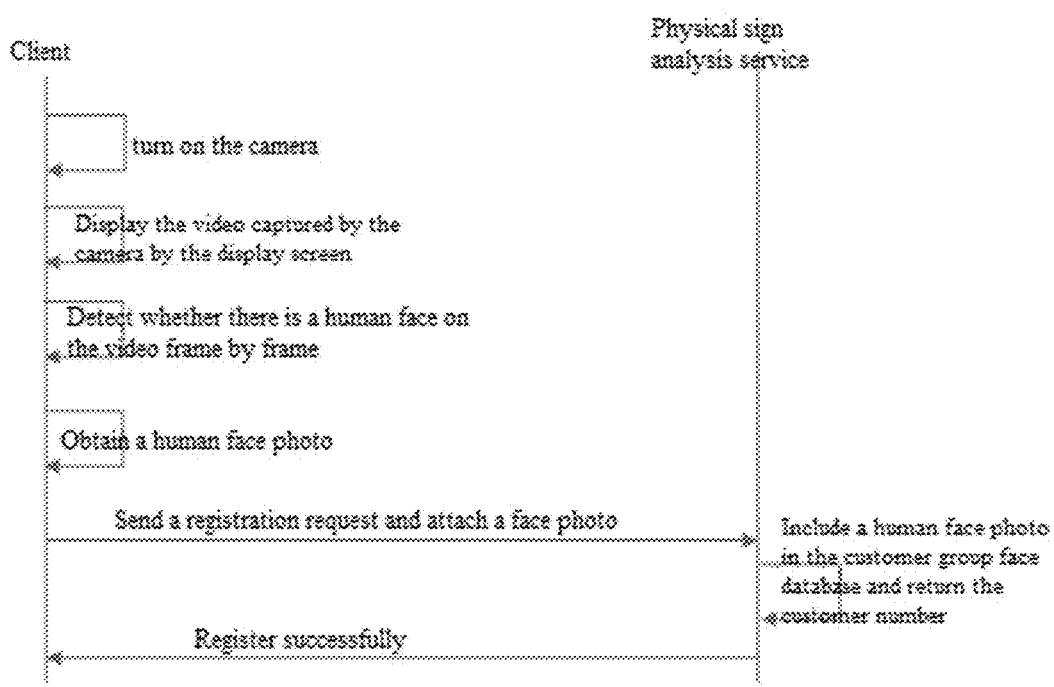
FIG. 7 is a flow diagram showing the registration of a client for physical sign analysis.

FIG. 7 shows the preparatory process for the front-end device to perform the physical sign analysis. This preparatory process is a registration process of the physical sign analysis by the front-end device, comprising:

(1) turning on the camera;

(2) displaying the video captured by the camera by the display screen;

(3) detecting whether there is a human face on the video frame by frame;

(4) obtaining a human face photo if a face is detected;

(5) sending a registration request to the physical sign analysis service by the client and attaching the obtained face photo;

(6) including the human face photo in the customer group face database by the physical sign analysis service, and returning the corresponding customer number to the client, to complete the registration successfully.

Figure 8:
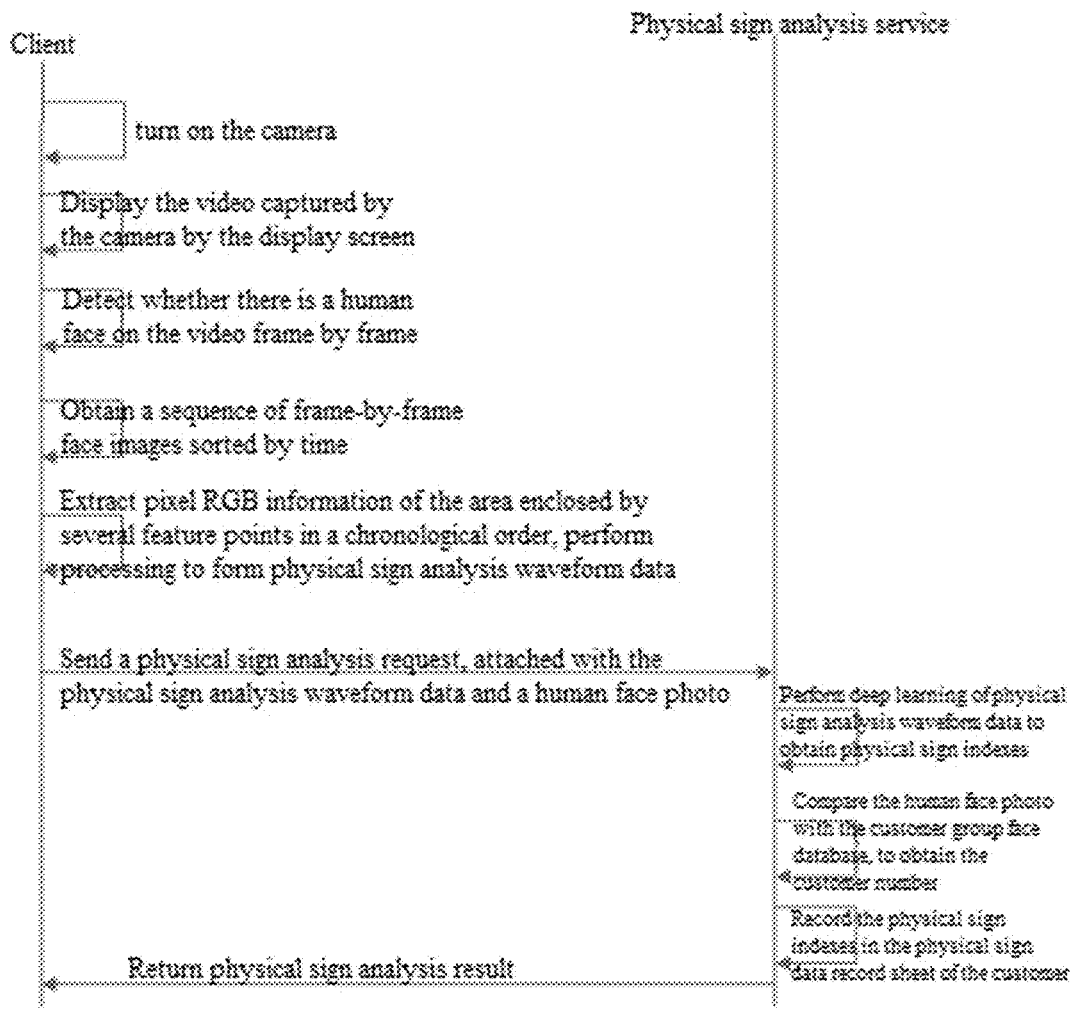
FIG. 8 is a flow diagram showing the physical sign analysis.

FIG. 8 shows the process of performing the physical sign analysis of the present invention, comprising:

(1) turning on the camera;

(2) capturing the video by the camera and sending to the processor, and displaying on the display device;

(3) performing human face detection analysis of the captured video frame by frame by the processor to detecting whether a human face exists, and acquiring the largest human face close to the middle position of the video only when detecting a human face;

(4) arranging frame-by-frame human face image sequences in a chronological order;

(5) extracting pixel RGB values of the area enclosed by several feature points in a chronological order and performing time series analysis to form physical sign analysis waveform data;

(6) sending a physical sign analysis request, attached with the physical sign analysis waveform data and a human face photo for analysis; sending the sign analysis waveform data and the human face images to the physical sign analysis service for deep learning of the relevant physical sign indexes to obtain relevant physical sign indexes of the person.

Figure 9:
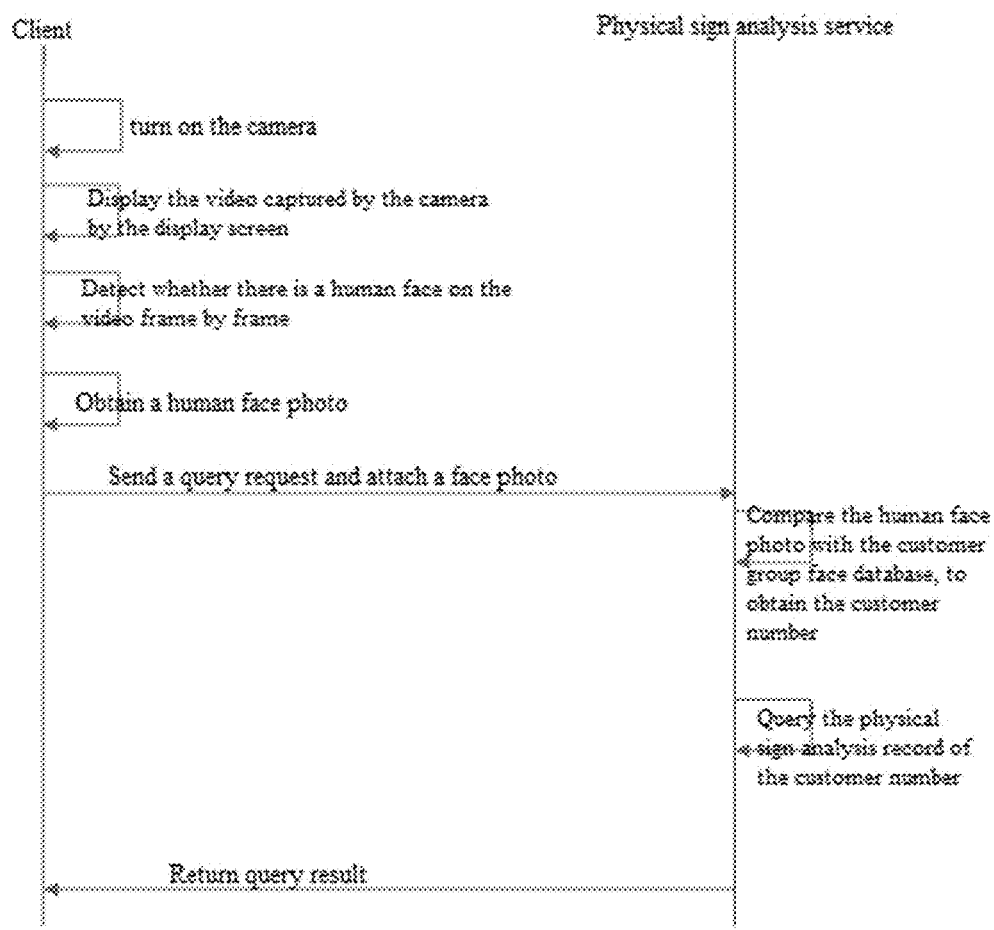
FIG. 9 is a flow chart for query.

FIG. 9 shows the query process in physical sign analysis service, comprising:

(1) turning on the camera;

(2) displaying, by the display screen, the video captured by the camera;

(3) detecting whether a human face exists frame by frame by the processor;

(4) obtaining a human face photo in the test result;

(5) sending a query request and attaching the obtained human face photo;

(6) comparing the human face photo with the customer group face database, to obtain the customer number;

(7) querying the physical sign analysis record of the customer number;

(8) returning the query result.

What is claimed is:

1. A system integrating video communication and physical sign analysis, comprising:
    at least one front-end device for receiving information and/or data that may exist at the front end;
    a mobile device, capable for interconnecting with the front-end device and establishing data communication;
    the front-end device and the mobile device can perform video communication, and the front-end device can perform physical sign analysis according to the images collected by a camera device;
    wherein during video communication, the front-end device or mobile device is the client of the video communication, and the client registers and maintains the registration status on the video communication;
    wherein the registration process of the client comprises:
    (1) assigning each client a unique client identification number;
    (2) initiating a registration application to the video communication service cloud when the client is running, and the registration application including registration information such as the client identification number and the client IP address of the current client;
    (3) generating a client status table by the video communication service cloud according to the registration information;
    (4) periodically sending heartbeat information to the video communication service cloud by the client, and refreshing the client status table by the video communication service cloud after receiving the heartbeat information;
    wherein the process of initiating video communication by the client comprises:
    (1) configuring a contact list on the client and binding a button to the contact persons in the contact list;
    (2) initiating a video communication connection request to another client through the video communication service cloud by the current client;
    (3) feeding back the current status information by another client, and feeding back the information of connection failure if the current status is in the call or during the call; and feeding back the information such as the IP address if the current status is no answer.

2. The system integrating video communication and physical sign analysis according to claim 1, wherein the front-end device comprises a camera device, a display device, an audio device, a button device and a processor, and the camera device, the display device, the audio device, and the button device are all connected to the processor and may perform data interaction with the processor.

3. The system integrating video communication and physical sign analysis according to claim 1, the processor can connect to the Internet network and perform data interaction with other devices via wired or wireless means.

4. The system integrating video communication and physical sign analysis according to claim 2, wherein the button device comprises a preset button and a physical sign analysis trigger button.

5. The system integrating video communication and physical sign analysis according to claim 2, wherein the camera device is a conventional camera having a certain resolution.

6. The system integrating video communication and physical sign analysis according to claim 2, wherein the display screen is an ordinary display screen or a touch display screen.

7. The system integrating video communication and physical sign analysis according to claim 2, wherein the process for the front-end device to perform physical sign analysis comprises:
   (1) capturing the video by the camera device and sending to the processor, and displaying on the display device;
   (2) performing human face detection analysis of the captured video frame by frame by the processor, and acquiring the largest human face close to the middle position of the video only;
   (3) positioning the coordinates of several feature points for the human face detected by each frame by algorithm;
   (4) extracting pixel RGB values of the area enclosed by several feature points for the human face image of each frame of the face in a time slice and performing time series analysis to form physical sign analysis waveform data;
   (5) sending the physical sign analysis waveform data and the human face images to the physical sign analysis service to obtain the relevant physical sign indexes of the person.

8. The system integrating video communication and physical sign analysis according to claim 7, further comprising a process of recording the physical sign indexes, specifically, comparing the current human face with the customer group face database to obtain the customer number, and recording the physical sign indexes obtained in the step (5) in the physical sign data record sheet of the customer number.

9. The system integrating video communication and physical sign analysis according to claim 1, wherein the initiator of the video communication is a front-end device or a mobile device.

10. The system integrating video communication and physical sign analysis according to claim 2, the processor can connect to the Internet network and perform data interaction with other devices via wired or wireless means.

* * * * *